United States Patent
Alchas et al.

(10) Patent No.: US 7,083,599 B2
(45) Date of Patent: Aug. 1, 2006

(54) PREFILLABLE INTRADERMAL DELIVERY DEVICE

(75) Inventors: Paul G. Alchas, Wayne, NJ (US); Carlos E. Guillermo, Clinton, CT (US); Philippe Emile Fernand Laurent, Oullins (FR); Marina S. Korisch, Wayne, NJ (US); Peter W. Heyman, Florham Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 215 days.

(21) Appl. No.: 10/721,844

(22) Filed: Nov. 25, 2003

(65) Prior Publication Data

US 2004/0116859 A1 Jun. 17, 2004

Related U.S. Application Data

(60) Division of application No. 09/835,248, filed on Apr. 13, 2001, now Pat. No. 6,776,776, which is a continuation-in-part of application No. 09/417,671, filed on Oct. 14, 1999, now Pat. No. 6,494,865.

(51) Int. Cl.
*A61M 5/32* (2006.01)
(52) U.S. Cl. ...................... 604/198; 604/117
(58) Field of Classification Search ........... 604/198, 604/117, 192, 187, 110, 263
See application file for complete search history.

(56) References Cited

U.S. PATENT DOCUMENTS

| | | |
|---|---|---|
| 1,934,046 A | 11/1933 | Demarchi |
| 2,876,770 A | 3/1959 | White |
| 3,400,715 A | 9/1968 | Pederson |
| 4,060,073 A | 11/1977 | Collica et al. |
| 4,270,537 A | 6/1981 | Romaine |
| 4,373,526 A | 2/1983 | Kling |
| 4,583,978 A | 4/1986 | Porat et al. |
| 4,596,556 A | 6/1986 | Morrow et al. |
| 4,769,003 A | 9/1988 | Stamler |
| 4,790,824 A | 12/1988 | Morrow et al. |
| 4,883,573 A | 11/1989 | Bruecken et al. |
| 4,886,499 A | 12/1989 | Cirelli et al. |

(Continued)

FOREIGN PATENT DOCUMENTS

DE 41 27 887 C1 1/1993

(Continued)

OTHER PUBLICATIONS

Article: Clinical Do's & Dont's—Giving Intradermal Injections by Edwina Mcconnell, RN, PhD.

(Continued)

*Primary Examiner*—Manuel Mendez
(74) *Attorney, Agent, or Firm*—Robert E. West

(57) ABSTRACT

An intradermal delivery device for use in intradermally injecting substances into the skin of an animal includes a needle cannula supported by a hub portion that is attachable to a prefillable container. A limiter portion surrounds the needle cannula and extends away from the hub portion toward a forward tip of the needle cannula. The limiter portion includes a skin engaging surface extending in a plane generally perpendicular to an axis of the needle cannula. The skin engaging surface is received against skin of an animal to administer an intradermal injection. The forward tip extends beyond the skin engaging surface a distance that enables penetration of the needle cannula into the dermis layer of the skin of the animal enabling injection of the substance into the dermis layer of the animal. The device includes enclosure means that is moveable for concealing the needle cannula after the injection has been administered.

30 Claims, 6 Drawing Sheets

U.S. PATENT DOCUMENTS

| | | | |
|---|---|---|---|
| 4,898,588 A | 2/1990 | Roberts | |
| 4,940,460 A | 7/1990 | Casey, I. et al. | |
| 4,941,880 A | 7/1990 | Burns | |
| 4,955,871 A | 9/1990 | Thomas | |
| 4,978,344 A | 12/1990 | Dombrowski et al. | |
| 5,015,235 A | 5/1991 | Crossman | |
| 5,064,413 A | 11/1991 | McKinnon et al. | |
| 5,071,353 A | 12/1991 | Van der Wal | |
| 5,141,496 A | 8/1992 | Dalto et al. | |
| 5,190,521 A | 3/1993 | Hubbard et al. | |
| 5,222,949 A | 6/1993 | Kaldany | |
| 5,295,975 A | 3/1994 | Lockwood, Jr. | |
| 5,312,335 A | 5/1994 | McKinnon et al. | |
| 5,331,954 A | 7/1994 | Rex et al. | |
| 5,334,144 A | 8/1994 | Alchas et al. | |
| 5,339,163 A | 8/1994 | Homma et al. | |
| 5,368,578 A | 11/1994 | Covington et al. | |
| 5,383,851 A | 1/1995 | McKinnon, Jr. et al. | |
| 5,417,662 A | 5/1995 | Hjerman et al. | |
| 5,431,155 A | 7/1995 | Marelli | |
| 5,437,647 A | 8/1995 | Firth et al. | |
| 5,466,220 A | 11/1995 | Brenneman | |
| 5,480,381 A | 1/1996 | Weston | |
| 5,496,286 A | 3/1996 | Stiehl et al. | |
| 5,503,627 A | 4/1996 | McKinnon et al. | |
| 5,514,107 A | 5/1996 | Haber et al. | |
| 5,520,639 A | 5/1996 | Peterson et al. | |
| 5,527,288 A | 6/1996 | Gross et al. | |
| 5,569,189 A | 10/1996 | Parsons | |
| 5,578,014 A | 11/1996 | Erez et al. | |
| 5,582,598 A | 12/1996 | Chanoch | |
| 5,599,302 A | 2/1997 | Lilley et al. | |
| 5,649,912 A | 7/1997 | Peterson | |
| 5,665,071 A | 9/1997 | Wyrick | |
| 5,702,362 A | 12/1997 | Herold et al. | |
| 5,704,911 A | 1/1998 | Parsons | |
| 5,779,677 A | 7/1998 | Frezza | |
| 5,873,856 A | 2/1999 | Hjertman et al. | |
| 5,879,327 A | 3/1999 | Moreau DeFarges et al. | |
| 5,891,085 A | 4/1999 | Lilley et al. | |
| 5,893,397 A | 4/1999 | Peterson et al. | |
| 5,921,963 A | 7/1999 | Erez et al. | |
| 5,957,897 A | 9/1999 | Jeffrey | |
| 5,961,495 A | 10/1999 | Walters et al. | |
| 5,993,412 A | 11/1999 | Deily et al. | |
| 6,001,089 A | 12/1999 | Burroughs et al. | |
| 6,004,299 A | 12/1999 | Arai et al. | |
| 6,036,675 A | 3/2000 | Thorne et al. | |
| 6,053,893 A | 4/2000 | Bucher | |
| 6,083,197 A | 7/2000 | Umbaugh | |
| 6,090,077 A | 7/2000 | Shaw | |
| 6,090,080 A | 7/2000 | Jost et al. | |
| 6,090,082 A | 7/2000 | King et al. | |
| 6,093,170 A | 7/2000 | Hsu et al. | |
| 6,099,504 A | 8/2000 | Gross et al. | |
| 6,112,743 A | 9/2000 | Denton | |
| 6,200,291 B1 | 3/2001 | DiPietro | |
| 6,436,068 B1 | 8/2002 | Bardy | |
| 6,494,865 B1* | 12/2002 | Alchas | 604/192 |

FOREIGN PATENT DOCUMENTS

| | | |
|---|---|---|
| EP | 0 279 583 B1 | 10/1993 |
| EP | 0 904 790 A2 | 3/1999 |
| FR | 612 401 A1 | 10/1926 |
| GB | 2 206 794 A | 1/1989 |
| JP | 2000-37456 | 2/2000 |
| WO | WO 95/01198 | 1/1995 |
| WO | WO 97/13537 | 4/1997 |
| WO | WO 97/37705 | 10/1997 |
| WO | WO 99/27986 | 6/1999 |
| WO | WO 99/34850 | 7/1999 |

OTHER PUBLICATIONS

Article: Dermal Immune System by Brian J. Nickoloff, MD, PhD.

Article: Injection Technique Intradermal.

Article: Intradermal Gene Immunization: The Possible Role of DNA Uptake in the Induction of Celluar Immunity to Viruses by Eyal Raz et al.

Article: Monographs of the Physiological Society No. 12: Substances Producing Pain and Itch by C.A. Keele and D. Armstrong Pub: The Williams & Wilkins Company (1964).

Article: The Dendritic Cell System and Its Role in Immunogenicity by Ralph Steinman.

Article: Trials of Intradermal Hepatitis B Vaccines in Gambian Children by Whittle, Lam, Ryder.

*Purified Influenza Vaccine: Clinical and Serologic Responses to Varying Doses and Different Routes of Immunization*, by C.A. Philips, B.R. Forsyth, W.A. Christmas, D.W. Gump, E.B. Whorton, I. Rogers, and A. Rudin, from the Department of Medicine and Community Medicine, University of Vermont College of Medicine, Burlington, Vermont.

*Polyvalent Influenza Vaccine: Comparison of Jet Injection with Intradermal and Subcutaneous Syringe Methods of Administration*, authored by Mervin L. Clark, Herbert Reinhardt, M. Clinton Miller, III and Ray Wilson, Oaklahoma City, Oklahoma.

*Experimental Comparison of Intradermal and Subcutaneous Vaccination with Influenza Vaccine*, from the American Journal of Medical Technology, vol. 31, Nov.-Dec. 1965, No. 6.

*Intradermal Influenza Immunization, Experience with Hong Kong Vaccine*, from the American Review of Respiratory Disease, vol. 103, 1971.

*Efficacy of Adsorbed Trivalent Split Influenza Vaccine Administered by Intradermal Route*, by I. Th. Niculescu, Eugenia Zilisteanu, V. Alexandrescu, Mihaela Matepluc, Ligia Cretescu, N. Ionescu, G. Molnar, R. Racasan and Adina Mogos, received for publication Dec. 4, 1980, from Arch. Roum. Path. Exq. Microbiol., T. 40, No. 1, pp. 67-70, Janvier-Mars, 1981.

*Efficacy of Intradermally Administered A2 Hong Kong Vaccine*, from Jama, from JAMA, Jul. 6, 1970, vol. 213, No. 1.

*Comparison of Responses to Influenza*, A-New Jersey/76-A/Victoria/75 *Virus Vaccine Administered Intradermally or Subcutaneously to Adults with Chronic Respiratory Disease*, authored by F. Alexander Herbert, R.P. Bryce Larke, and Edythe L. Markstad, from the Journal of Infectious Diseases, vol. 140, No. 2, Aug. 1979.

*A Comparison of the Intradermal and Subcutaneous Routes of Influenza Vaccination with A/New Jersey/76 (Swine Flu) and A/Victoria/75: Report of a Study and Review of the Literature*, by William Halperin, MD, MPH, William I. Weiss, MD, Ronald Altman, MD, MPH, Michael A. Diamond, MD, Kenneth J. Black, BA, Alfred W. Iaci, BBA, MS, Henry C. Black, DVM and Martin Goldfield, MD, from the ALPHA Dec. 1979, vol. 69, No. 12.

*Effect of Dosage and Route of Inoculation Upon Antigenicity of Inactivated Influenza Virus Vaccine (Hong Kong Strain) In Man*, from Bull. Org. mond. Santé Bull. Wld Hlth Org. 1969, 41, 507-516.

*Comparative Analysis of Six European Influenza Vaccines*, from Eur. J. Clin. Microbiol. Infect. Dis. 1996, 15:121-127.

*Morphological and Biochemical Characterization of Influenza Vaccines Commercially Available in the United King-*

*dom*, by F. Renfrey and A. Watts, from Vaccine 1994, vol. 12, No. 8.

*Influenza Immunization Policies and Practices in Japan*, from the Journal of Infectious Diseases, vol. 141, No. 2, Feb. 1980.

*Clinical Immunogenicity and Tolerance Studies of Liquid Vaccines Delivered by Jet-Injector and a New Single-Use Cartridge (Imule®): Comparison with Standard Syringe Injection*, authored by Isabelle Parent du Chatelet, Jean Lang, Martin Schlumberger, Emmanuel Vidor, Georges Soula, Alain Gene, Steven M. Standaert, Pierre Saliou and Imule® Investigators Group, Vaccine 1997, vol. 15, No. 4.

Abstract: *Does a Needleless Injection System Reduce Anxiety in Children Receiving Intramuscular Injections?*, by Polillio AM, Kiley J, from the Pediatric Primary Care Clinic, Boston City Hospital, MA, USA, Pediatr. Nurs. 1997, Jan.-Feb.; 23(1): 46-9.

Abstract: *Intradermal Administration of Viral Vaccines*, by Nagafuchi S., Kashiwagi S, Imayama S, Hayashi J, Niho Y, from Rev. Med. Virol. Apr. 1998; 8(2):97-111.

Abstract: *Letter: Intradermal Influenza Vaccination*, by Payler DK, Skirrow MB, Br Med J Jun. 29, 1974; 2(921);727.

Intradermal Influenza Vaccination; British Medical Journal, Jun. 29, 1974.

Smith Kline Beecham Meeting Agenda.

* cited by examiner

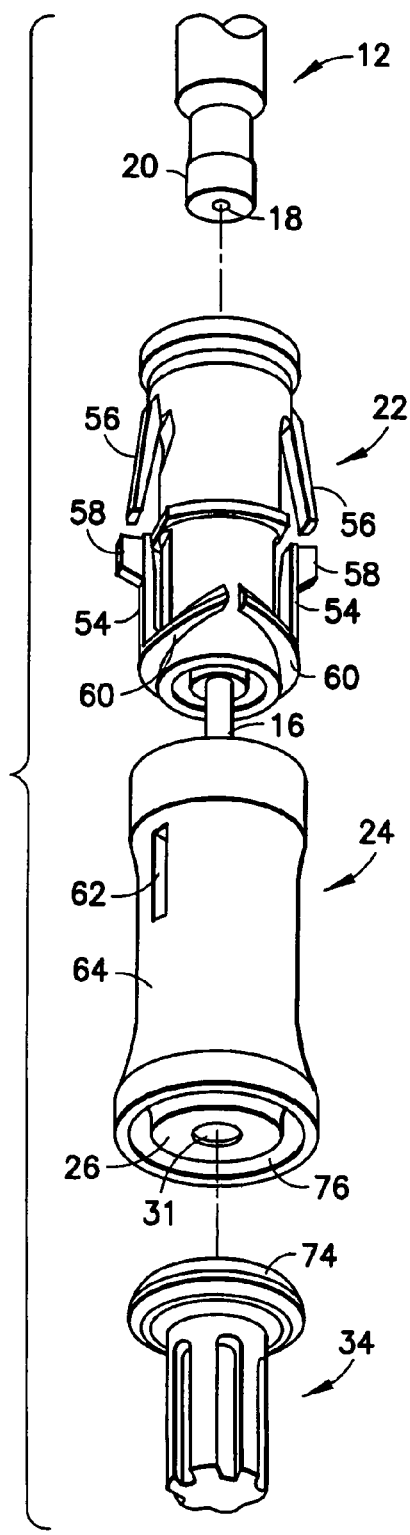
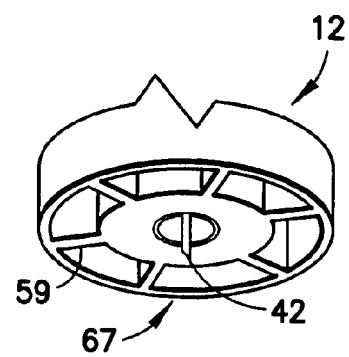
FIG.3B
FIG.3A

PREFILLABLE INTRADERMAL DELIVERY DEVICE

CROSS-REFERENCE TO RELATED APPLICATIONS

This application is a division of U.S. patent application Ser. No. 09/835,248, filed on Apr. 13, 2001, now U.S. Pat. No. 6,776,776, which is a continuation-in-part of U.S. patent application Ser. No. 09/417,671 filed on Oct. 14, 1999, now U.S. Pat. No. 6,494,865.

FIELD OF THE INVENTION

The present invention relates generally to delivery devices for delivering substances such as drugs, vaccines and the like, and more specifically relates to a drug delivery device having a needle cannula and a limiter for engaging the surface of the skin and limiting penetration of the tip of the needle cannula into the skin. More specifically, the present invention relates to a limiter capable of fixing the orientation of the needle cannula in a generally perpendicular plane to the skin engaging surface of the limiter and capable of enclosing the needle cannula subsequent to administering the intradermal injection.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown that hepatitis B vaccines administered intradermally are more immunogenic if administered intramuscularly. In addition, substances have been injected intradermally for diagnostic testing, such as, for example using what is known in the art as the "Mantoux test" to determine the immunity status of the animal against tuberculosis and the immediate hypersensitivity status of Type I allergic diseases.

An intradermal injection is made by delivering the substance into the epidermis and upper layers of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 50–200 microns, and the dermis, the inner and thicker layer of the skin, has a thickness between 1.5–3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as a "wet injection" because of reflux of the substance from the injection site.

The standard procedure for making an intradermal injection is known to be difficult to perform, and therefore dependent upon experience and technique of the healthcare worker. This procedure is recommended to be performed by stretching the skin, orienting the bevel of a 26 Gauge short bevel needle cannula upwardly and inserting the needle cannula to deliver a volume of 0.5 ml or less of the substance into the skin of an animal with the needle cannula being inserted into the skin at an angle varying from around 10–15 degrees relative to the plane of the skin to form a blister or wheal in which the substance is deposited or otherwise contained. Accordingly, the technique utilized to perform the standard intradermal injection is difficult and requires the attention of a trained nurse or medical doctor. This procedure also makes it essentially impossible to self-administer an intradermal injection. Inserting the needle to a depth greater than about 3.0 mm typically results in a failed intradermal injection because the substance being expelled through the cannula will be injected into the subcutaneous tissue of the animal. Further, the standard method is not suitable for self-administration of intradermal injections.

Further, with the advent of viral infections that are transferred through contact with bodily fluids, it is desirable to enclose or conceal a needle cannula subsequent to administering an injection. Preferably, a delivery device should include a mechanism that is capable of enclosing a needle cannula immediately subsequent to administering the injection. If a needle is left uncovered for even a short period of time after administering an injection, such as, for example, while trying to reattach a needle cap, a biohazard exists. Therefore, it is desirable to provide an intradermal delivery device with a means for enclosing the needle cannula that is simply designed, easy to use, and readily available immediately after administering an injection.

Accordingly, there has been a need for a delivery device providing the ability of performing an intradermal injection of substances which overcomes the problems and limitations associated with conventional devices which may also be self-administered. Further, there has been a need to provide the delivery device with the ability to enclose a needle cannula immediately subsequent to administering the intradermal injection. The combination of these two features in the same delivery device would provide the ability to both reduce the probability of error and pain caused from the intradermal injection and to conceal the needle cannula after the injection has been administered.

SUMMARY OF THE INVENTION AND ADVANTAGES

In contrast to the devices discussed above, the present invention both enables the administration of an intradermal injection utilizing a simplified method that reduces the probability of error and also enables the user to enclose the needle immediately after administering the injection.

An intradermal delivery device for use in intradermally injecting substances into the skin of an animal includes a prefillable reservoir adapted to contain the substance. An outlet port is in fluid communication with the reservoir. A needle cannula is in fluid communication with the outlet port and includes a forward tip extending away from the delivery device. The forward tip is adapted for penetrating the skin of an animal. A limiter portion surrounds the needle cannula and includes a generally flat skin engaging surface extending in a plane generally perpendicular to an axis of the needle cannula. A hub portion is secured around the needle cannula and defines a locator for the limiter to position the limiter upon the device. The skin engaging surface is adapted to be placed against skin of an animal to administer an intradermal injection of the substance. The forward tip of the cannula extends beyond the skin engaging surface a distance equal to approximately 0.5 mm to 3 mm such that the limiter limits penetration of the needle cannula to the dermis layer of the skin of the animal thereby enabling injection of the substance into the dermis layer of the animal. An enclosure means encloses the needle cannula following the intradermal injection.

The present invention provides the desirable features set forth above that are not presently included together on the same needle assembly. The limiter allows an intradermal injection to be made at a generally perpendicular angle to the angle to the skin of the animal and then also encloses the needle subsequent to administering the injection.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3A is an exploded view of the inventive limiter and hub;

FIG. 3B is a perspective view of an alternative skin engaging surface;

DETAILED DESCRIPTION OF THE PREFERRED EMBODIMENT

Figure 1:
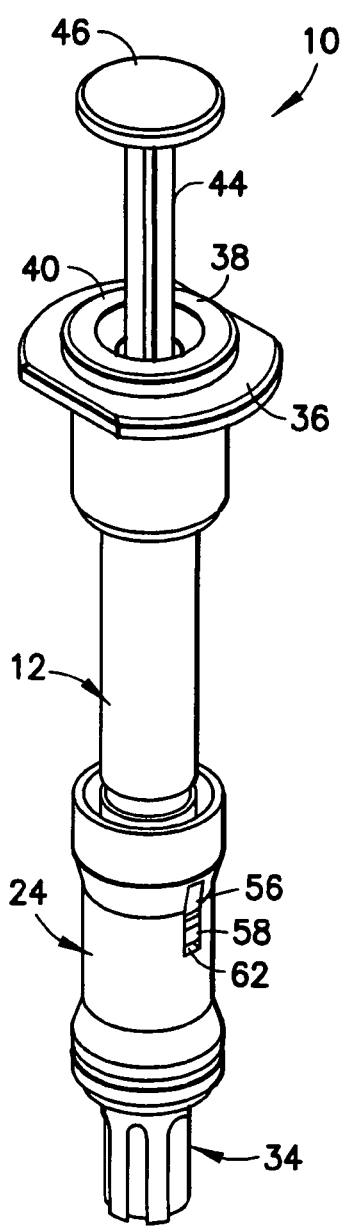
FIG. 1 is a perspective view of the intradermal delivery device of the present invention.
Figure 2:
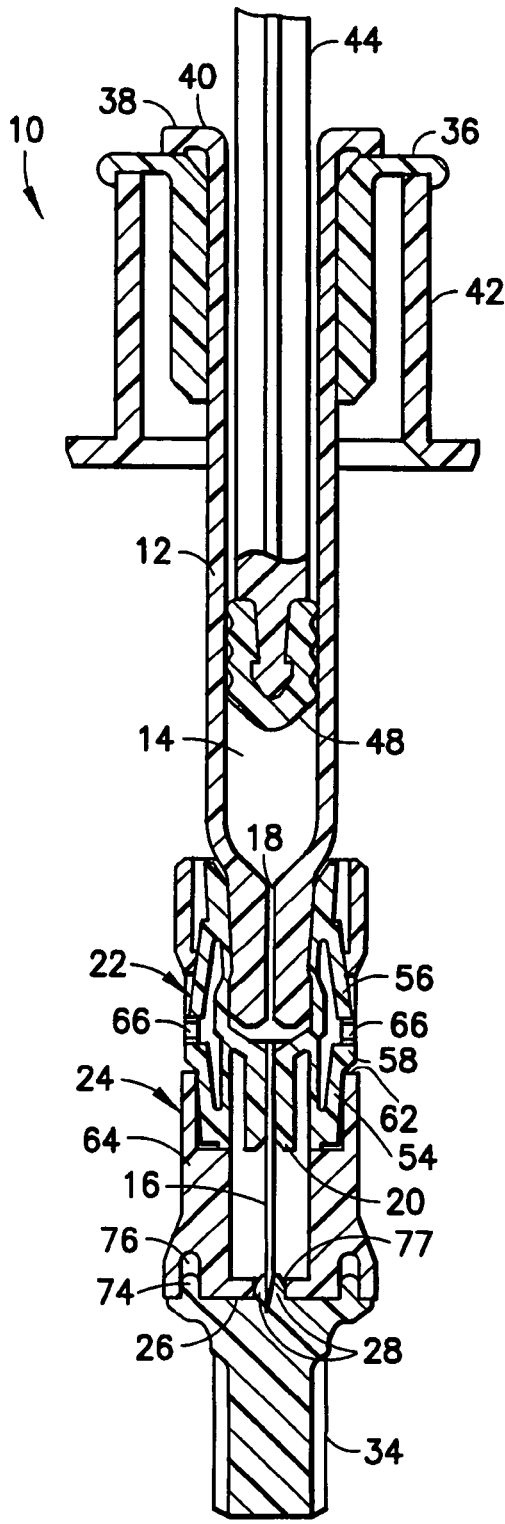
FIG. 2 is a side sectional view of the intradermal delivery device of the present invention showing a hypodermic needle assembly.

Referring to FIGS. 1 and 2, an intradermal delivery device for injecting substances into the skin of an animal is generally shown at 10. The device includes a prefillable container 12 having a reservoir 14 for storing substances intended for injection into the skin of an animal. These substances include vaccines and certain medicaments and drugs. Additionally, these substances can be used for diagnostic testing such as, for example, the Mantoux test to determine immunity status against tuberculosis and immediate hypersensitivity status of Type I allergic diseases.

Also, the substance intradermally delivered in accordance with the method of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, *cholera*, cocaine addiction, diphtheria, tetanus, HIB, Lyme disease, meningococcus, measles, mumps, *rubella, varicella*, yellow fever, Respiratory syncytial virus, tick borne japanese encephalitis, pneumococcus, streptococcus, typhoid, influenza, *hepatitis*, including *hepatitis* A, B, C and E, otitis media, rabies, polio, HIV, parainfluenza, rotavirus, Epstein Barr Virus, CMV, chlamydia, non-typeable haemophilus, *moraxella* catarrhalis, human papilloma virus, *tuberculosis* including BCG, gonorrhoea, asthma, atheroschlerosis malaria, *E-coli*, Alzheimers, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

A needle cannula 16 is in fluid communication with an outlet port 18 that leads to the reservoir 14. The outlet port 18 allows for the substance to be expelled from the prefillable container 12 through a receiver 20 disposed at the end of the prefillable container 12. The needle cannula 16 is inserted through a hub portion 22, which is secured to the receiver 20 through a variety of known manners. In one example, an interference fit is provided between the interior of the hub 22 and the exterior of the receiver 20. In another example, a conventional luer fit arrangement is provided to secure the hub 22 to the end of the prefillable container 12. As can be appreciated, a needle assembly designed according to this invention is readily adapted to a wide variety of conventional syringe styles.

Figure 4:
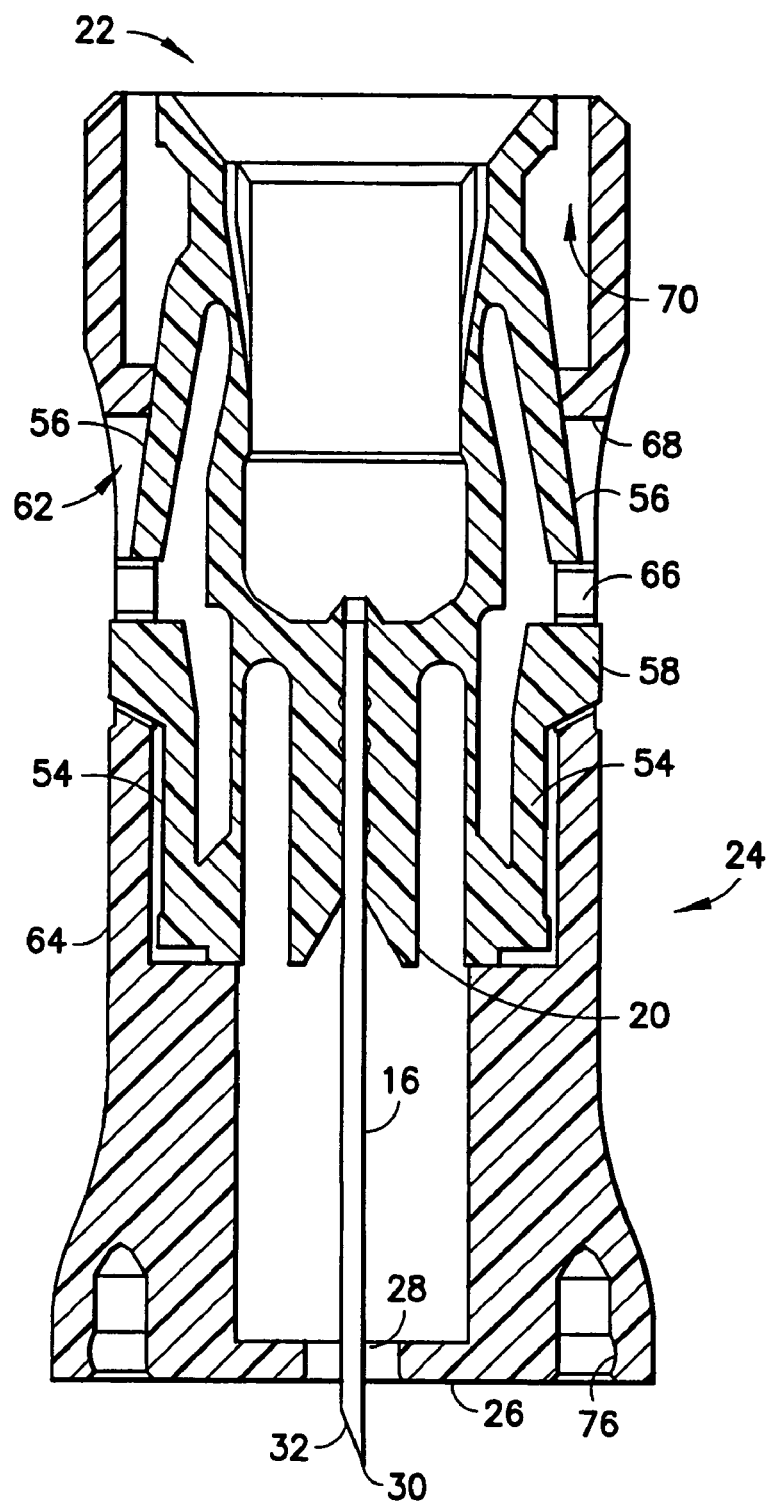
FIG. 4 is a side sectional view of the needle assembly showing the forward tip exposed for administering an intradermal injection.
Figure 5:
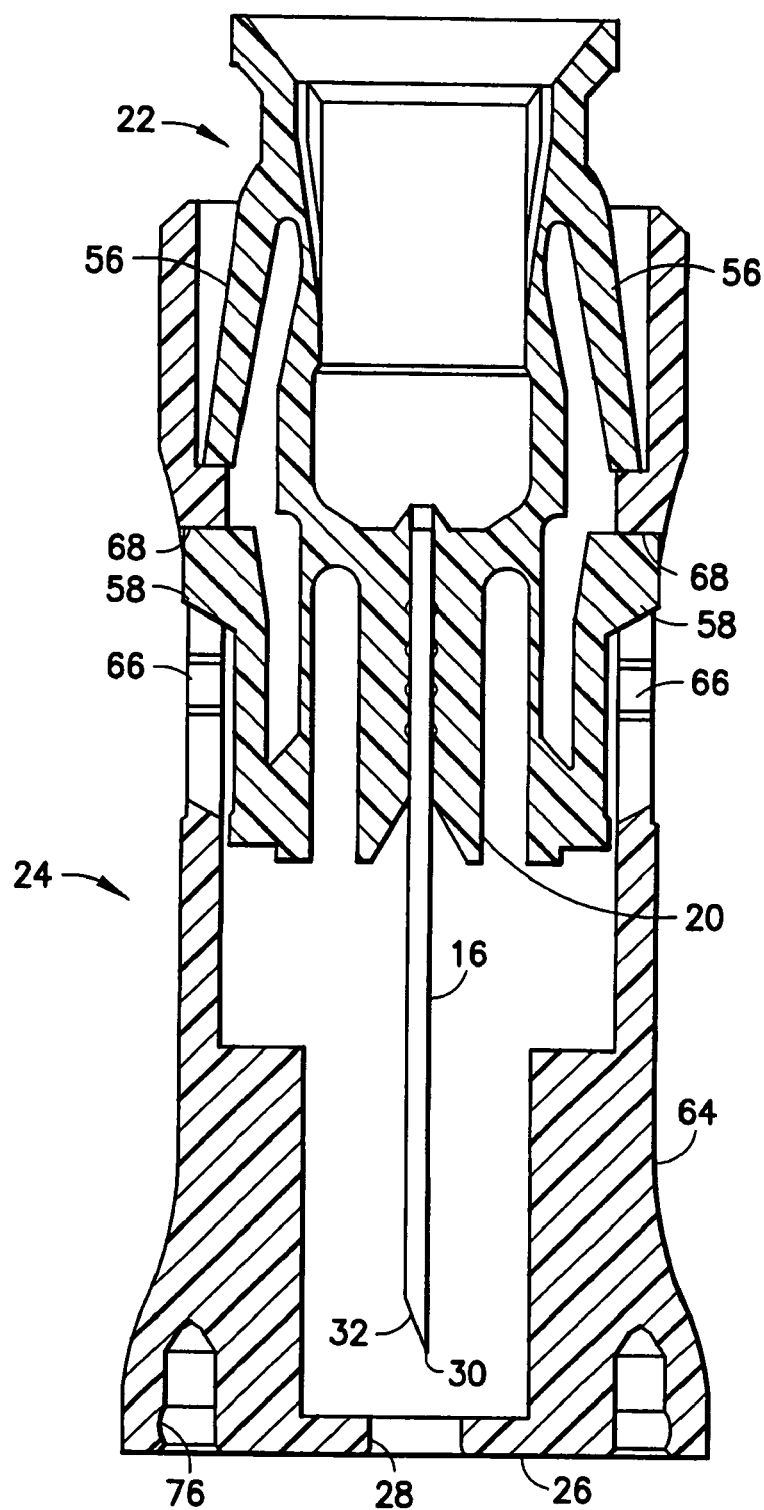
FIG. 5 is a side sectional view of the needle assembly showing the forward tip retracted into the limiter to conceal the needle cannula.

Alternatively to affixing the needle cannula 16 to the receiver 20, the needle cannula 16 can be affixed to the hub 22 prior to attaching the hub 22 to the receiver 20. A limiter 24 surrounds the needle cannula 16 and includes a generally flat skin engaging surface 26 extending in a plane generally perpendicular to an axis of the needle cannula 16 with about fifteen degrees or more preferably with about five degrees. The skin engaging surface 26 is best seen in FIGS. 4 and 5. The flat skin engaging surface 26 stabilizes the intradermal delivery device during injection and thus preferably has a cross-sectional dimension of at least 5 mm or between 5 and 20 mm. The limiter 24 includes a needle opening 28, which closely receives a forward tip 30 of the needle cannula 16 extending therethrough (FIG. 4). The dimensional relationship between the needle opening 28 and the forward tip 30 can be controlled depending on the needs of a particular situation. The forward tip 30 extends away from the skin engaging surface 26 a distance from approximately 0.5 mm to approximately 3 mm. Therefore, the skin engaging surface 26 limits the depth the needle cannula 16 can penetrate into the skin of the animal. Further, an elastomeric insert or septum 31 may be inserted centrally in the skin engaging surface 26 in which case the needle cannula 16 pierces the elastomeric surface when attaching the limiter 24 to the hub 22 (FIG. 3). The elastomeric insert functions as an assembly aid so that the needle cannula 16 does not need to be threaded through the needle opening 28.

The forward tip 30 includes a beveled edge 32 angled such that the length of the forward tip 30 is reduced from that of a standard hypodermic needle tip. Preferably, the beveled edge 32 ranges in length between approximately 0.8 mm and 1.0 mm. More preferably, the beveled edge 32 includes a length of approximately 0.9 mm. A standard beveled tip length ranges from approximately 1.3 mm to 1.6 mm. The reduced length of the present beveled edge 32 reduces the potential of the needle cannula 16 passing through the dermis layer of the skin of the animal and resulting in the substance from the reservoir 14 being injected into the subcutaneous region of the animal.

A cap 34 is positioned adjacent the skin engaging surface 26 to cover the forward tip 30 of the needle cannula 16. Preferably, the cap 34 is formed from an elastomeric material or thermoplastic elastomer that would allow the forward tip 30 to penetrate the cap surface and thus be sealed by the cap 34. Accordingly, the cap 34, by sealing the needle cannula 16, seals the reservoir 14 preventing the substance from leaking from the reservoir 14 through the needle cannula 16 prior to administering the intradermal injection.

Referring to FIG. 2, an adapter 36 is fixed to a flange 38 disposed on an opposite end of the prefillable container 12 from the receiver 20. A plurality of snaps 40 clasp the flange 38 to secure the adapter 36 to the prefillable container 12. The adapter 36 provides an engagement surface for the prefillable container 12 to be stored in a tray 42 used for processing and shipping the intradermal delivery device 10. A plunger 44 includes an activation flange 46 at one end and a stopper 48 at an opposite end as is known in the art. The stopper 48 is slidably disposed within the reservoir 14 and is selectively actuated to expel the substance from the reservoir 14 through the needle cannula 16. Therefore, to administer an intradermal injection, the skin engaging surface 26 of the limiter 24 is pressed against the skin of the animal causing the needle cannula 16 to penetrate the skin and the activation flange or end 46 on the plunger 44 is depressed to expel the solution from the reservoir 14.

In a preferred embodiment, the limiter 24 functions as an enclosure to conceal or enclose the needle cannula 16 after an intradermal injection has been administered. Therefore, as shown in FIG. 4, the limiter 24 is located in a first position 50 exposing the forward tip 30 enabling an intradermal injection to be administered. FIG. 5 shows the limiter located in a second position 52 in which the needle cannula 16 is fully retracted inside the limiter 24 preventing any further access to the needle cannula 16 after an intradermal injection has been administered.

Referring now to FIG. 3A, the hub 22 includes at least one locking finger 54 and at least one stop 56. Preferably, the limiter 24 includes two each of the locking finger 54 and the stop 56. Each locking finger 54 is cantilevered in a direction opposite the direction of the forward tip 30. Each stop 56 is cantilevered in a direction that is the same as the direction of the forward tip 30. Each locking finger 54 includes a tab 58, the purpose of which will be described further hereinbelow. Each locking finger 54 is attached to the hub 22 proximate to a helical rib 60 that centers the hub 22 inside the limiter 24. However, it is not necessary that the locking fingers 54 be attached to the limiter 24 proximate to the helical rib 60, which is only illustrated by way of example. The limiter 24 defines at least one slot 62 oriented generally parallel to the needle cannula 16 in a wall 64 of the limiter 24. A protuberance 66 is disposed on one side of the slot 62, the purpose of which will become evident further below.

Each tab 58 is received by the slot 62 when the hub 22 is inserted into the limiter 24. The protuberance 66 is positioned between each locking finger 54 and stop 56 when the limiter 24 is located in the first position 50. The tab 58 abuts the protuberance 66 in each slot 62 providing enough resistance to the limiter 24 sliding upon the hub 22 to insert the needle cannula 16 in to the skin of the animal and administer the intradermal injection. The tabs 58 are snappable over the protuberance 66 to move the limiter 24 from the first position 50 to the second position 52 subsequent to administering the intradermal injection.

To move the limiter 24 from the first position 50 to the second position 52, the prefillable container 12 is pulled away from the limiter 24 as though trying to separate the prefillable container 12 from the limiter 24. Under sufficient separating force, the tabs 58 will snap over the protuberances 66 allowing the stops 56 to move outwardly from the inside of the limiter 24. A rib 68 circumscribes the inner surface 70 of the limiter 24 and functions as a catch (FIG. 4). Each tab 58 prevents the hub 22 from being removed from the limiter 24 by engaging a back end of the slot 62. Upon passing the rib 68, each stop 56 expands into the inner surface 70 disposed inside the limiter 24 and engage the rib 68 thereby preventing the limiter 24 from being moved from the second position 52 to the first position 50. Accordingly, the needle cannula 16 is secured inside the limiter 24 and cannot be exposed once the limiter 24 has been moved to the second position 52.

Referring to FIGS. 2 and 3A, the cap includes an annular shaped ring 74 disposed upon a surface that abuts the skin engaging surface 26 of the limiter 24. The ring is aligned coaxially with the needle cannula 16 and is received within an annular groove 76 disposed within the skin engaging surface 26. In the preferred embodiment, the outer dimension or diameter of the cap is equal to or less than the receiver 20. The ring 74 snaps into the annular groove 76 securing the cap 34 to the limiter 24. A tip bulge 77 (FIG. 2) is received by the needle opening 28 in the skin engaging surface 26. The forward tip 30 of the needle cannula 16 penetrates the tip bulge 77 sealing the needle cannula 16 and preventing the substance from leaking out of the reservoir 14 through the needle cannula 16. FIG. 3B shows an alternative skin engaging surface 67 as having a plurality of spokes 59 projecting outwardly from the axis formed from the needle cannula 16.

Figure 6:
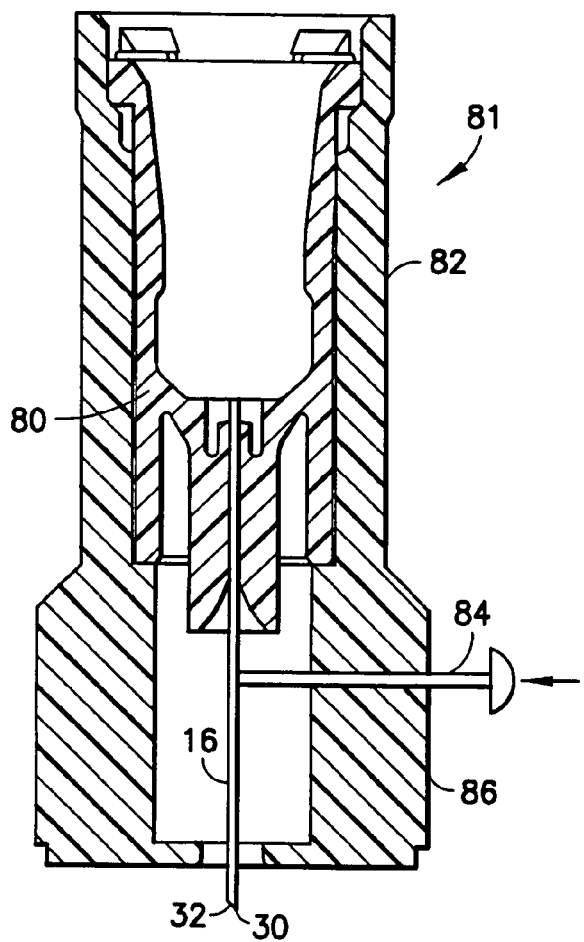
FIG. 6 is a side sectional view of an alternative embodiment of the needle assembly showing the forward tip exposed for administering an intradermal injection.
Figure 7:
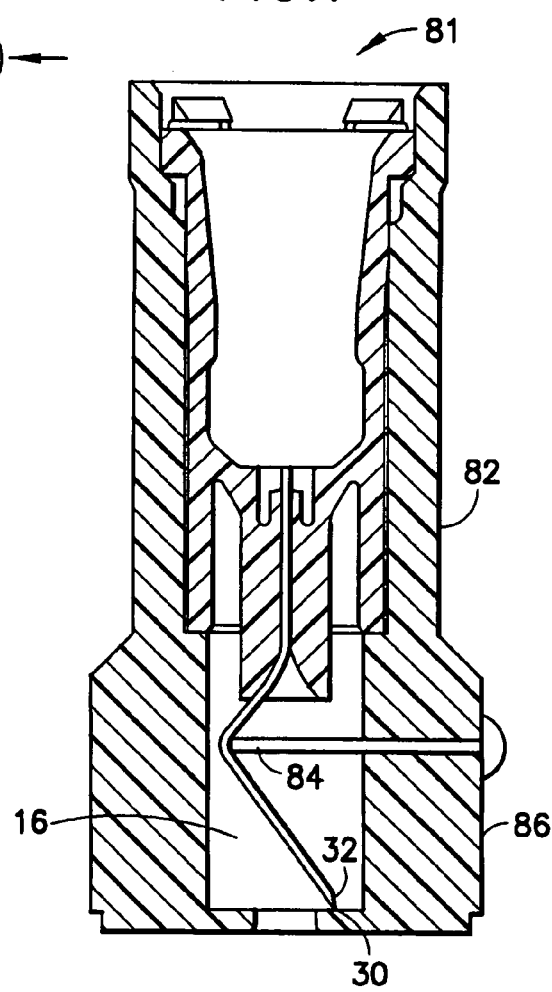
FIG. 7 is a side sectional view of the alternative embodiment of the needle assembly showing the forward tip retracted into the limiter to conceal the needle cannula.

An alternate embodiment is generally shown in FIGS. 6 and 7 at 81. In this embodiment, an alternative hub 80 secures an alternative limiter 82 in the same fashion as that described in the preferred embodiment. The alternative limiter 82 is stationary on the alternative hub 80 and is not moved into a first or second position. A needle plunger 84 is inserted through an alternative limiter wall 86 at an angle generally perpendicular to the needle cannula 16. The needle plunger 84 is retained in the wall 86 either through a friction fit, or an equivalent that allows the needle plunger 84 to be forced inwardly of the alternative limiter 82. As shown in FIG. 7, the needle plunger 84 functions as the needle cannula enclosure when pushed inwardly of the alternate limiter 82 in which case the needle cannula 16 is bent and therefore retracted into the limiter 82 preventing exposure to the needle cannula 16 subsequent to administering an intradermal injection.

Figures 8A, 8B:
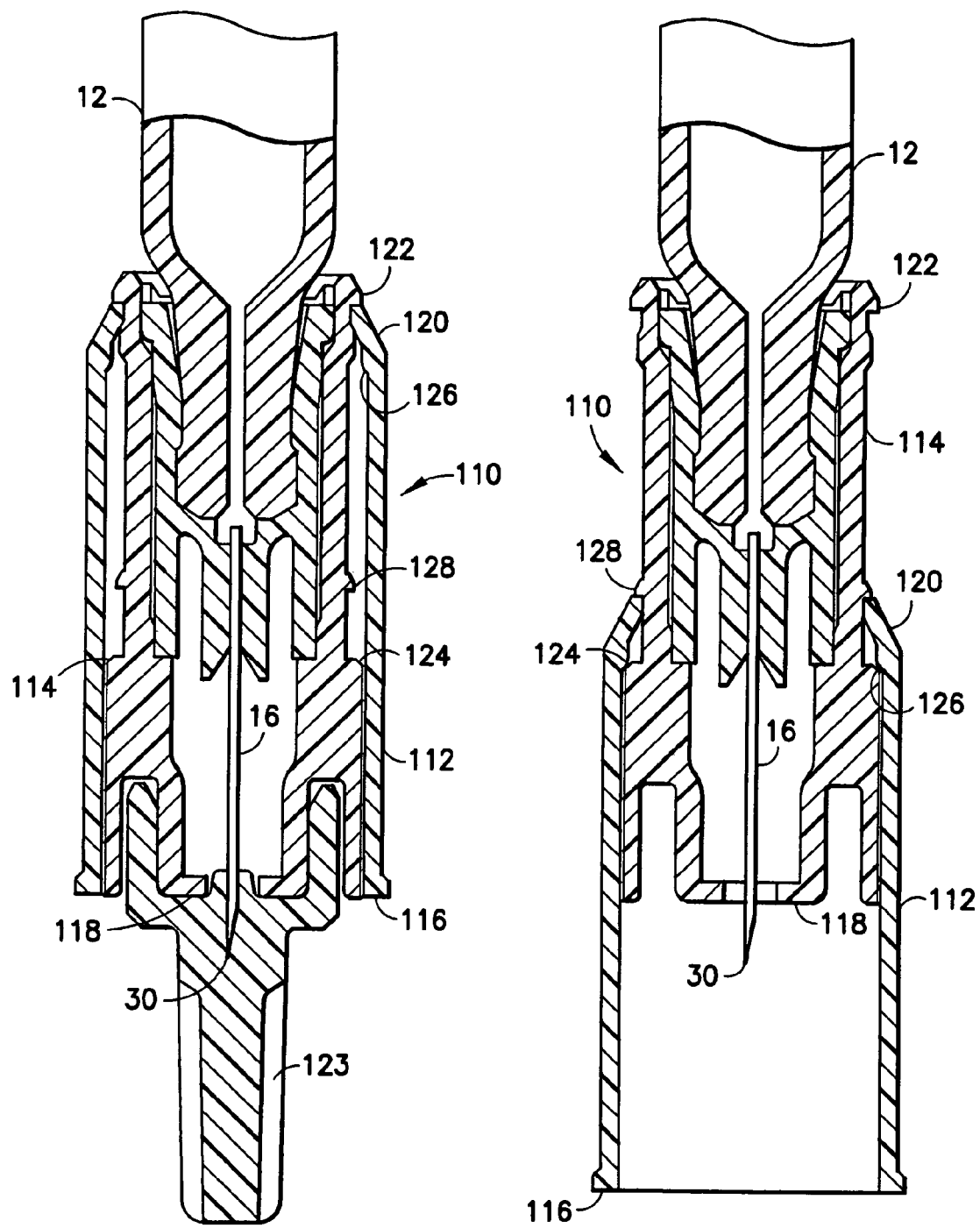
FIG. 8A is a side sectional view of an alternative embodiment of the needle assembly showing the inventive sleeve.
FIG. 8B is a side sectional view of the inventive sleeve enclosing the needle cannula.

Referring to FIG. 8A an alternate assembly 110 adapted to enclose the needle cannula 16 subsequent to administering an intradermal injection is shown. A sleeve 112 generally defining a tube slidably circumscribes the limiter 114. The sleeve 112 includes a skin engaging end 116 that is aligned in generally the same plane as the skin engaging surface 118 when the assembly 110 is prepared for administering the intradermal injection. A rearward end 120 of the sleeve 112 is tapered inwardly towards the axis of the needle cannula 16. The rearward end 120 abuts a rear flange 122 or the limiter 114, which prevents the sleeve 112 from being removed from the limiter 114 in the direction of the prefillable container 12. In this embodiment, an elastomeric tip cap 123 is removably secured to the skin engaging surface 118 and receives the forward tip 30 of the needle cannula 16.

Subsequent to administering the intradermal injection, the sleeve 112 may be manually pulled in the direction of the forward tip 30 of the needle cannula 16 as shown in FIG. 8B. The limiter 114 includes a sleeve stop 124, which engages a corresponding contour 126 disposed on an inside surface of the sleeve 112 thereby preventing the sleeve from being removed from the limiter 114. At least one ramp 128 is disposed upon an outer surface of the limiter 114 over which the rearward end 120 of the sleeve 112 slides when the sleeve 120 is moved to cover the forward tip 30 of the needle cannula 16. The ramp 128 prevents the sleeve 112 from being moved toward the prefillable container 12 re-exposing the forward tip 30 once the rearward end 120 of the sleeve 112 has been slid past the ramp 128 to enclose the needle cannula 16.

As will now be understood, the intradermal delivery device of this invention includes a needle enclosure means which encloses or conceals the needle cannula tip following injection and which preferably cannot be retracted to prevent accidental needle contact or reuse. In one embodiment shown in FIGS. 4 and 5, the limiter 24 may be extended following injection and locked in place. In a second embodiment shown in FIGS. 6 and 7, the needle cannula 16 is bent or deformed beyond its elastic limit by plunger 82 to permanently enclose the tip portion 30 within the limiter 82. In a third embodiment shown in FIGS. 8A and B, the assembly includes an extendable shield 112, which locks in the extended position, preventing contact with the needle. Alternatively, the needle assembly may be retractable as disclosed, for example, in a copending application Ser. No. 09/834,669, filed Apr. 13, 2001 entitled "Prefillable Intradermal Injector," the disclosure of which is incorporated by reference.

When the hub portion 22 and limiter 24 are attached to the front end of a prefillable container 12 in the form of a syringe barrel, the assembled device 10 is preferably supplied to the pharmaceutical industry in sterile, clean, ready to fill packaging to facilitate processing. This processing includes filling and stoppering while the device 10 is suspended in a nest (not shown). However, the diameter of the limiter 24 is significantly greater than the diameter of the 0.4 ml or 0.5 ml syringe barrel and the barrel flanges, from which the barrels are normally suspended in the nest. Thus, the nest typically used for this small barrel size has holes (chimneys) which are too small for the limiter 24 to pass through, and a nest normally used for a larger barrel (1–3 ml) must be employed.

To prevent the device 10 from falling through this nest, the flanges of the syringe barrel must be increased in diameter through the addition of the adapter 36. In addition, the chimneys of the nest serve the function of centering the device below the filling nozzles and stopper insertion tubes on automated filling machines. If the devices 10 are not centered properly, the filling nozzle can hit the side of the syringe barrel while moving into the barrel at the start of the filling process, resulting in damage to the nozzle, inaccurate fill volumes, potential glass breakage or particulate contamination when the syringe barrel is formed of glass, or wetting of the barrel inner wall above the area which will subsequently be stoppered. This could compromise the sterility seal created between the stopper ribs and barrel wall, compromising sterility. During the stoppering operation, where centering is even more critical, poor centering can result in damage to the stainless steel insertion tube, glass breakage, or stoppers being placed crookedly (or not at all) in the barrel, resulting in a poor seal.

With the small diameter syringe barrel placed in the larger than normal diameter nest chimneys, the chimneys lose their centering function as the barrels are free to move in a large radius. Therefore, the diameter of the barrel must be built up so that it is only marginally smaller than the inner diameter of the chimney. This is accomplished by the addition of the adapter 36, preferably made of plastic, slid on from the tip end of the barrel, before attaching the hub portion 22 and limiter 24, or snapped on from the side of the syringe barrel.

To minimize the number of parts to be added to the syringe barrel, the flange extending features required above are incorporated with the diameter increasing features to form one component referred to as the adapter 36 or a barrel spacer.

Several lengths are possible for the adapter 36. A short adapter 36 provides the two functions mentioned previously. A longer adapter (not shown) also can serve as a labeling surface, as an alternative to placing the label directly on the outer diameter of the syringe barrel. The larger diameter adapter permits the use of a larger label and thereby permits information to be incorporated on the label. The upper limit to the length of the adapter 36 is determined by the volume of liquid substances placed in the syringe barrel and the length of the stopper. GMPs require that injectable liquid substances be 100% inspected for particulate contamination, and this is conducted either visually by operators or using automated vision systems, both of which require an unobstructed, 360 degree view of the liquid substance. In addition, the stopper must be inspected for the presence of liquid trapped between the ribs, potentially compromising sterility. Thus, the adapter 36 must end at a point beyond the back end of the stopper, allowing a clear view of both the liquid substance and the stopper.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A delivery device for use in injecting medical substances into the skin of an animal, comprising:
   a prefillable container adapted for storing a medical substance;
   a needle cannula attached to said delivery device and having a forward tip extending away from said delivery device;
   a hub portion secured around said needle cannula;
   a limiter portion surrounding said needle cannula and extending away from said hub portion toward said forward tip of said needle cannula, said limiter portion including a generally flat skin engaging surface extending in a plane generally perpendicular to an axis of said needle cannula and being adapted to be received against skin of an animal to administer an intradermal injection of the substance, said forward tip extending beyond said skin engaging surface length of approximately 0.5 mm to approximately 3 mm, wherein said limiter portion limits penetration of said needle cannula into the dermis layer of the skin of the animal thereby injecting substance into the dermis layer of the animal;
   wherein said hub portion defines a locator for said limiter thereby positioning said limiter upon said device; and
   an enclosure means for concealing said needle cannula after administering said intradermal injection.

2. A device as set forth in claim 1 wherein said enclosure means comprises said limiter, which is slidably disposed upon said hub having at least a first position and a second position, said first position exposing said forward tip of said needle cannula and said second position concealing said forward tip of said needle cannula.

3. A device as set forth in claim 2 wherein said enclosure means comprises a needle plunger inserted through said limiter and being depressable for bending said needle cannula beyond its elastic limit thereby retracting said needle cannula into said limiter.

4. A device as set forth in claim 3 wherein said needle plunger is oriented generally perpendicular to said needle cannula.

5. A device as set forth in claim 2 wherein said hub portion is attachable to an outlet port of said prefillable container.

6. A device as set forth in claim 2 further including a cap positioned adjacent said skin engaging surface thereby concealing said forward tip of said needle cannula wherein said cap has an outside dimension equal to or less than said limiter.

7. A device as set forth in claim 6 wherein said cap comprises an elastomeric material.

8. A device as set forth in claim 6 wherein said forward tip of said needle cannula penetrates said cap thereby sealing said needle cannula.

9. A device as set forth in claim 2 wherein said limiter includes at least one slot oriented generally parallel to said needle cannula and having a protuberance disposed on one side thereof.

10. A device as set forth in claim 9 wherein said hub includes at least one locking finger and at least one stop, said at least one locking finger cantilevered away from said forward tip and said at least one stop being cantilevered toward said forward tip.

11. A device as set forth in claim 10 wherein said at least one locking finger includes a tab received by said slot in said limiter.

12. A device as set forth in claim 11 wherein said tab is snappable over said protuberance for moving said limiter from said first position to said second position.

13. A device as set forth in claim 12 wherein said protuberance is disposed between said tab and said at least one stop when said limiter is located in said first position.

14. A device as set forth in claim 13 wherein said limiter includes a catch engaging said at least one stop when said limiter is in said second position thereby preventing said limiter from being moved into said first position from said second position.

15. An intradermal delivery device for injecting substances into the skin of an animal, comprising:
   a prefillable container having a reservoir adapted to contain a selected substance and an outlet port that allows the substance to be expelled from said reservoir during an injection;
   a needle cannula in fluid communication with said outlet port and having a forward tip adapted to penetrate the skin of an animal;
   a limiter surrounding said needle and having a generally flat skin engaging surface extending in a plane generally perpendicular to an axis of said needle cannula adapted to be placed against the skin of the animal to administer an intradermal injection of the substance, said needle forward tip extending away from the said skin engaging surface from approximately 0.5 mm to approximately 3 mm such that said limiter limits penetration of said forward tip into the dermis layer of the skin of the animal thereby injecting the substance into the dermis layer of the animal; and
   an enclosure means moveable to conceal said needle cannula.

16. The device as set forth in claim 15 wherein said prefillable container comprises a syringe having a generally hollow, cylindrical body portion and a plunger received within said reservoir, said plunger being selectively movable within said reservoir thereby causing the substance to be forced out of said outlet port while administering an intradermal injection.

17. The device as set forth in claim 16 including a hub portion supporting said needle cannula and being selectively secured to said prefillable container near said outlet port.

18. A device as set forth in claim 17 wherein said enclosure means comprises said limiter, which is slidably disposed upon said hub having at least a first position and a second position, said first position exposing said forward tip of said needle cannula and said second position concealing said forward tip of said needle cannula.

19. A device as set forth in claim 18 wherein said limiter defines at least one slot oriented generally parallel to said needle cannula and having a protuberance disposed on one side thereof.

20. A device as set forth in claim 19 wherein said hub includes at least one locking finger and at least one stop, said at least one locking finger cantilevered away from said forward tip and said at least one stop being cantilevered toward said forward tip.

21. A device as set forth in claim 20 wherein said at least one locking finger includes a tab received by said slot in said limiter.

22. A device as set forth in claim 21 wherein said tab is snappable over said protuberance for moving said limiter from said first position to said second position.

23. A device as set forth in claim 22 wherein said protuberance is disposed between said tab and said at least one stop when said limiter is located in said first position.

24. A device as set forth in claim 23 wherein said limiter includes a catch engaging said at least one stop when said limiter is in said second position thereby preventing said limiter from being moved into said first position from said second position.

25. A device as set forth in claim 15 wherein said enclosure means comprises a needle plunger inserted through said limiter and being depressable for bending said needle cannula thereby retracting said needle cannula into said limiter.

26. A device as set forth in claim 25 wherein said needle plunger is oriented generally perpendicular to said needle cannula.

27. A device as set forth in claim 15 further including a removable cap positioned adjacent said skin engaging surface thereby concealing said forward tip of said needle cannula having an outside dimension equal to or less than said limiter.

28. A device as set forth in claim 27 wherein said cap comprises an elastomeric material.

29. A device as set forth in claim 28 wherein said forward tip of said needle cannula penetrates said cap thereby sealing said needle cannula and preventing the substance from leaking from said reservoir.

30. A device as set forth in claim 15 wherein said hub defines a locator for said limiter thereby positioning said limiter upon said assembly.

* * * * *